(12) United States Patent
Cush et al.

(10) Patent No.: US 8,685,887 B2
(45) Date of Patent: Apr. 1, 2014

(54) SURFACTANT COMPOSITIONS

(75) Inventors: Randall Charles Cush, Basel (CH); Sarah Beth Cush, Basel (CH); Michael James Hopkinson, Greensboro, NC (US); Jason Keiper, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 110 days.

(21) Appl. No.: 12/933,910

(22) PCT Filed: Mar. 23, 2009

(86) PCT No.: PCT/US2009/037934
§ 371 (c)(1), (2), (4) Date: Dec. 20, 2010

(87) PCT Pub. No.: WO2009/120621
PCT Pub. Date: Oct. 1, 2009

(65) Prior Publication Data
US 2011/0105332 A1    May 5, 2011

Related U.S. Application Data

(60) Provisional application No. 61/139,118, filed on Dec. 19, 2008.

(51) Int. Cl.
| | | |
|---|---|---|
| *A01N 63/00* | (2006.01) | |
| *A01N 33/00* | (2006.01) | |
| *A01N 47/28* | (2006.01) | |
| *A01N 57/00* | (2006.01) | |
| *A01N 37/10* | (2006.01) | |
| *A01N 37/12* | (2006.01) | |
| *A61K 31/215* | (2006.01) | |
| *A61K 31/235* | (2006.01) | |
| *A61K 31/22* | (2006.01) | |
| *B01D 17/00* | (2006.01) | |
| *C07C 39/18* | (2006.01) | |
| *C07C 211/00* | (2006.01) | |
| *C07F 9/02* | (2006.01) | |

(52) U.S. Cl.
USPC ........... 504/118; 504/127; 504/148; 504/194; 504/326; 514/506; 514/529; 514/532; 514/551; 516/135; 564/463; 568/17; 568/716; 568/780

(58) Field of Classification Search
USPC .......... 504/118, 127, 148, 194, 326; 516/135; 564/463; 568/17, 716, 780; 514/506, 514/529, 532, 551
See application file for complete search history.

(56) References Cited

U.S. PATENT DOCUMENTS

| | | | |
|---|---|---|---|
| 7,883,715 B2 * | 2/2011 | Abraham et al. | 424/405 |
| 2003/0050194 A1 | 3/2003 | Hopkinson et al. | |
| 2006/0252648 A1 | 11/2006 | Bell et al. | |
| 2007/0184983 A1 * | 8/2007 | Finch et al. | 504/328 |

FOREIGN PATENT DOCUMENTS

CN    1903036 A *   1/2007   ............ A01N 43/88

* cited by examiner

*Primary Examiner* — Jane C Oswecki
(74) *Attorney, Agent, or Firm* — James Cueva

(57) ABSTRACT

The present application relates to surfactant compositions comprising a) at least one phosphated arylphenol alkoxylate surfactant having an average degree of alkoxylation of from 4-8; and b) at least one alkylamine alkoxylate surfactant having an average degree of alkoxylation of from 2-12 and to the use of these compositions in pesticide formulations comprising solid or encapsulated pesticidally active ingredients or formulation aids and methods for improving the re-suspension properties of pesticide suspensions.

31 Claims, No Drawings

SURFACTANT COMPOSITIONS

This application is a 371 of International Application No. PCT/US2009/037934 filed Mar. 23, 2009, which claims priority to U.S. 61/039,118 filed Mar. 25, 2008, the contents of which are incorporated herein by reference.

BACKGROUND

The present application relates to surfactant compositions comprising a) at least one phosphated arylphenol alkoxylate surfactant having an average degree of alkoxylation of from 4-8; and b) at least one alkylamine alkoxylate surfactant having an average degree of alkoxylation of from 2-12 and to the use of these compositions in pesticide formulations comprising solid or encapsulated pesticidally active ingredients or formulation aids.

Numerous agrochemical formulations comprise solid or encapsulated pesticidally active ingredients or formulation aids which remain insoluble upon dilution in a liquid carrier, for example, water. Examples of these formulation types include capsule suspensions, oil dispersions, oil flowables, suspension concentrates, suspoemulsions and mixtures thereof.

Pesticide concentrates containing solid or encapsulated pesticidally active ingredients or formulation aids may exhibit settling of the suspended or dispersed components over time. This settling can lead to the creation of hard packed sediment making it difficult to get the materials out of the container. In many cases, the pesticide solids or encapsulated pesticides may stay suspended in the formulated concentrate but upon dilation of these types of formulations, the suspended or dispersed solids will settle with time to the bottom of a container. The rate of sedimentation depends on as number of factors such as particle size, particle concentration, viscosity of the suspending medium and the specific gravity difference between the particles and the suspending medium. Once settled, the sediments may become hard packed in nature, making redispersion or resuspension extremely difficult. The creation of hard packed sediment can occur when the tanks are not agitated. Interruptions in the spray schedule frequently occur due to normal breaks, for example overnight, taken by the applicator, weather changes, mechanical malfunction or unforeseen events which result in non-agitation of the spray tank.

SUMMARY OF THE INVENTION

There is now provided compositions comprising a) at least one phosphated arylphenol alkoxylate surfactant having an average degree of alkoxylation of from 4-8; and b) at least one alkylamine alkoxylate surfactant having an average degree of alkoxylation of from 2-12.

There is also provided pesticide formulations comprising solid or encapsulated pesticidally active ingredients or formulation aids and a surfactant composition comprising a) at least one phosphated arylphenol alkoxylate surfactant having an average degree of alkoxylation of from 4-8; and b) at least one alkylamine alkoxy late surfactant having an average degree of alkoxylation of from 2-12.

One embodiment relates to a composition comprising i) a liquid continuous phase, ii) a surfactant composition comprising a) at least one phosphated arylphenol alkoxylate surfactant having an average degree of alkoxylation of from 4-8; and b) at least one alkylamine alkoxylate surfactant having an average degree of alkoxylation of from 2-12 and iii) a dispersed phase comprising at least one solid or encapsulated pesticidally active ingredient or formulation aid.

One embodiment relates to a method for improving the re-suspension properties of a pesticide suspension comprising forming a composition comprising at least one solid or encapsulated pesticidally active ingredient or formulation aid and a surfactant composition comprising a) at least one phosphated arylphenol alkoxylate surfactant having an average degree of alkoxylation of from 4-8; and b) at least one alkylamine alkoxylate surfactant having an average degree of alkoxylation of from 2-12, wherein said composition re-suspends more readily than a similarly formulated composition which does not comprise said surfactant composition.

These and other benefits will be evident from the detailed description that follows.

DETAILED DESCRIPTION OF THE PRESENT INVENTION

The compositions of the present invention comprise a) at least one phosphated arylphenol alkoxylate surfactant having an average degree of alkoxylation of from 4-8; and at least one alkylamine alkoxylate surfactant having an average degree of alkoxylation of from 2-12.

The phosphated arylphenol alkoxylate surfactants consist of one or more compounds of formula

wherein $R^1$ is a substituted phenoxy;

Z is —$CHR^2CHR^3$—O—, where $R^2$ and $R^3$, which may be the same or different, are hydrogen or methyl;

a is 4 to 8 b is 1 or 2; and

A is a phosphate radical or salts thereof.

In one embodiment, $R^1$ is substituted by two or three 1-phenylethyl groups. Preferably, $R^1$ is a tri-substituted phenoxy, substituted by a 1-phenylethyl radical at the 2, 4 and 6 positions and Z is —$CH_2CH_2$—O—. In the art, this compound is known as a phosphated tristyrylphenol ethoxylate.

The phosphated arylphenol alkoxylate surfactants may be produced by condensation of alkylene oxide with an aryl phenol, followed by phosphation to give an anionic surfactant. Phosphation can be performed by methods known to one of ordinary skill, for example, reacting the alkoxylated alcohol with either phosphorous pentoxide or poly phosphoric acid. The diester content of the phosphated arylphenol alkxoylates, i.e., when 'b' is 2, may range anywhere from 0 to 100% by weight of the phosphated arylphenol alkoxylates.

The phosphated arylphenol alkoxylates may also contain free nonionic surfactant as a side product of the surfactant production product. Thus, the non-ionic surfactant content of the phosphated arylphenol alkoxylate surfactant may range anywhere from 0 to 50 percent. Further, the addition of non-ionic arylphenol alkoxylate surfactants, above the amount of non-ionic arylphenol alkoxylate surfactant present as a side product of the anionic surfactant production, is also contemplated.

The alkylamine alkoxylate surfactants comprise (i) an amine having the formula

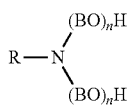

where R represents a straight- or branched-chain alkyl or alkenyl group having from about 8 to about 22 carbon atoms, B represents an alkylene group, for example an ethylene or propylene group, and n and n' are integers such that n+n' has a value of about 2 to about 12, (ii) a mixture of such amines having different groups R, the average number of carbon atoms in the groups R being from about 8 to about 22, or (iii) a mixture of such amines having different values of n and n', n and n' being integers such that the average value of n+n' in the mixture is about 2 to about 12, R having a single value or an average value as in a mixture (ii).

Commercially available amine surfactants within the above formula are often mixtures rather than single compounds. They include alkoxylated derivatives of "cocoamine" in which the groups R correspond to alkyl groups derived from various fatty acids including myristic, lauric, palmitic and stearic acids. The average number of carbon atoms in R in cocoamine is 12-14. Other examples are alkoxylated derivatives of "oleylamine", where the principal carbon chain of R corresponds to that of oleic acid (18 carbon atoms), and of "tallowamine" where R is mainly a mixture of hexadecyl and octadecyl. Such commercial surfactants are also usually mixtures of molecules having various values of n+n', and surfactants having a low average value of n+n' may contain a minor proportion of non-alkoxylated or mono-alkoxylated amines. The preferred alkoxylated derivatives are the ethoxylated derivatives.

In a preferred embodiment alkylamine alkoxylate surfactants are those where B represents an ethylene group, and those where the number or average number of carbon atoms in the group or groups R is from about 10 to about 20. As regards the value or average value of n+n', in preferred surfactants this lies in the range from 2 to 12. Specific examples of preferred surfactants are ethoxylated derivatives of cocoamine, tallowamine and oleylamine where in each case n+n' has an average value of from 2 to 12, more preferably from 2 to 8.

In one embodiment, the alkylamine alkoxylate surfactant is an alkylamine ethoxylate having an average degree of ethoxylation of 2 to 8. In a preferred embodiment, the alkylamine ethoxylate surfactant comprises cocoamine ethoxylate having an average degree of ethoxylation of 2 to 8. In a preferred embodiment, the alkylamine ethoxylate surfactant comprises tallowamine ethoxylate having an average degree of ethoxylation of 2 to 12.

In one embodiment, there is provided pesticide formulations comprising solid or encapsulated pesticidally active ingredients or formulation aids and a surfactant composition comprising a) at least one phosphated arylphenol alkoxylate surfactant having an average degree of alkoxylation of from 4-8; and b) at least one alkylamine alkoxylate surfactant having an average degree of alkoxylation of from 2-12.

In one embodiment, there is provided a composition comprising i) a liquid continuous phase, ii) a surfactant composition comprising a) at least one phosphated arylphenol alkoxylate surfactant having an average degree of ethoxylation of from 4-8; and b) at least one alkylamine alkoxylate surfactant having an average degree of alkoxylation of from 2-12 and iii) a dispersed phase comprising at least one solid or encapsulated pesticidally active ingredient or formulation aid.

The compositions of the present invention can comprise concentrated formulations containing solid or encapsulated pesticidally active ingredients and/or formulation aids and a surfactant composition comprising a) at least one phosphated arylphenol alkoxylate surfactant having an average degree of ethoxylation of from 4-8; and b) at least one alkylamine alkoxylate surfactant having an average degree of alkoxylation of from 2-12. Preferably, the solid or encapsulated pesticidally active ingredients and/or formulation aids are suspended or dispersed in the concentrated formulation. The concentrated formulations include capsule suspensions, oil dispersions, oil flowables, suspension concentrates, suspoemulsions and mixtures thereof.

In one embodiment, the pesticide formulation is obtained by diluting a concentrated formulation comprising at least one solid or encapsulated pesticidally active ingredient in a suitable amount of liquid carrier to obtain the desired concentration of the at least one solid or encapsulated pesticidally active ingredient, wherein surfactants a) and b), individually, are present in the concentrated formulation, added separately to the diluted formulation or liquid carrier or a combination thereof.

In one embodiment, the surfactants a) and b) are present in the concentrated formulation. In another embodiment, at least one of surfactants a) or b) is added to the liquid carrier and at least some amount of the surfactants a) or b) added to the liquid carrier is not present in the concentrated formulation. For example, at least one of the surfactants a) and b) may be present in a separate container and used as a tank mix additive.

Depending on the product, the amounts of components a) and b) can vary widely. Component a) is present in an amount of 0.0001 to 95% by weight; and component b) is present in an amount of 0.0001 to 95% by weight. The amounts of components a) and b) required will vary based on the nature, for example particle size, hyrdrophobicity etc., and amount of the solid or encapsulated pesticidally active ingredients and/or formulation aids present in the composition. In a preferred embodiment, components a) and b) are present in a ratio of 20:1 to 1:20, preferably 4:1 to 1:4.

In one embodiment, the composition of the present invention comprises a surfactant concentrate comprising surfactants a and b). In a preferred embodiment, the concentrate of surfactants a) and b) is substantially free, preferably free, of pesticides. In this surfactant concentrate, surfactants a) and b) together are present in an amount of from 20 to 100% by weight of the concentrate. In one embodiment, the surfactant concentrate is added to a container, for example a spray tank, before, after or simultaneously with a pesticidal composition comprising solid and/or encapsulated pesticidally active ingredients or formulations aid, and before, after or simultaneously with the addition of a carrier, preferably water.

In one embodiment, the composition of the present invention comprises a pesticidal concentrate comprising at least one solid or encapsulated pesticidally active ingredient or formulation aid and a surfactant concentrate comprising surfactants a) and b). In this pesticidal concentrate, surfactants a) and b) together are preferably present in an amount of from 0.01 to 60% by weight of the concentrate.

In one embodiment, the composition of the present invention comprises a diluted composition, such as a pesticidal composition in a spray tank, comprising at least one solid or encapsulated pesticidally active ingredient or formulation aid and a surfactant concentrate comprising surfactants a) and b).

In this diluted composition, surfactants a) and b) together are preferably present in an amount of from 0.0001 to 10% by weight of the diluted composition.

A method for improving the re-suspension properties a pesticide suspension comprising forming a composition comprising at least one solid or encapsulated pesticidally active ingredient or formulation aid and a surfactant composition comprising a) at least one phosphated arylphenol alkoxylate surfactant having an average degree of alkoxylation of from 4-8; and b) at least one alkylamine alkoxylate surfactant having an average degree of alkoxylation of from 2-12, wherein said composition re-suspends more readily than a similarly formulated composition which does not comprise said surfactant composition.

A method for improving the re-suspension properties of a pesticide suspension wherein a surfactant composition comprising a) at least one phosphated arylphenol alkoxylate surfactant having an average degree of alkoxylation of from 4-8; and b) at least one alkylamine alkoxylate surfactant having an average degree of alkoxylation of from 2-12, or at least one component thereof, is present in a concentrate comprising the solid or encapsulated, pesticidally active ingredient or formulation aid.

A method for improving the re-suspension properties of a pesticide suspension wherein a surfactant composition comprising a) at least one phosphated arylphenol alkoxylate surfactant having an average degree of alkoxylation of from 4-8; and b) at least one alkylamine alkoxy late surfactant having an average degree of alkoxylation of from 2-12 is added to a dilute composition comprising the solid or encapsulated, pesticidally active ingredient formulation aid.

Solid pesticidally active ingredients or formulation aids suitable for use in the present invention include those solid components that remain dispersed or suspended in the formulation, including the diluted composition. Although the pesticidally active ingredients or formulation aids may exhibit some solubility in the carrier, preferably water, typically the pesticidally active ingredients or formulation aids will be substantially insoluble in the selected carrier. These substantially insoluble pesticidally active ingredients and/or formulation aids may sometimes be referred to herein for brevity as a "water-insoluble" active ingredients or formulation aids even if they have measurable solubility in the selected carrier. When the carrier is water, these active ingredients and/of formulation aids preferably have a solubility in water at 20° C. not greater than about 5000 mg/l as measured at the pH of the aqueous phase of the pesticidal composition. It will be apparent to one skilled in the art that the solubility in water of some active ingredients depends on pH if they have a titratable acid or base functionality; specifically acids are more soluble above their pKa and bases are more soluble below their pKb. Thus acids may be rendered insoluble in water for the purposes of the present discussion if the aqueous phase is maintained at a pH close to or below their pKa, even if they may be more soluble than about 5000 mg/l at a higher pH. Especially preferred water-insoluble active ingredients useful in the present invention have a solubility in the aqueous phase at 20° C. not greater than about 2000 mg/l.

Any solid or encapsulated pesticidally active ingredient and/or formulation aid present in an amount sufficient to settle and create hard packed sediment is suitable for use in the present invention. Stable suspensions of pesticide particles in a fluid, such as suspension concentrates (SC), are becoming a very popular type of formulation. For example, The Pesticide Manual 13$^{th}$ Edition (British Crop Protection Council) has 275 entries for SC products.

Suspension concentrates are usually made by premixing the active ingredient powder in an aqueous solution Of a wetting agent and a dispersing agent, followed by a wet grinding process in a bead mill to give the desired particle size. The general requirements of an active ingredient to be suitable for formulation as a suspension concentrate are high melting point, preferably greater than 80° C., low solubility in water, and chemical stability in water. Representative solid pesticidally active ingredients include azoxystrobin; chlorothalonil; fludioxonil; isoxaflutole; mesotrione; including salts and chelates thereof; PPO inhibitors such as butafenacil; prodiamine; triazines such as atrazine, simazine and terbuthylazine; and thiabendazole.

Encapsulated pesticidally active ingredients are well known in the art. Microencapsulated formulations comprise products where the biologically active material is surrounded by a barrier or membrane or polymeric or similar material in order to give controlled or delayed release of active ingredient. This treatment often also gives benefits in operator and environmental safety and tank mix compatibility.

A common formulation of this type is a microcapsule suspension (CS) in which small spherical particles, typically 0.1-20 μm in diameter, composed of a core material of active ingredient and an outer shell wall of polymeric material are suspended in water. Other microencapsulated formulation types include capsule suspensions for seed treatment (CF), encapsulated granules (CG), mixed formulations of CS and SC (ZC), mixed formulations of CS and suspoemulsions (ZE) and mixed formulations of CS and oil-in-water emulsions (ZW).

The nature of the encapsulation is not critical to the present invention nor is the nature and properties of the pesticidally active ingredient which is encapsulated. Methods of encapsulating active ingredients is well known to one of ordinary skill in the art and include preparation of microcapsule suspensions by interfacial polymerization for example by reaction of oil-soluble and water-soluble monomers at the oil-water emulsion interface, in-situ polymerization or an aminoplast pre-polymer process; preparation of microcapsules by coacervation; preparation of solid microcapsules by spray encapsulation; preparation of microcapsules by cooling melted dispersions; and preparation of microcapsules by solvent evaporation.

Suitable wall materials are known to those of ordinary skill in the art and include polyurea, polyamide, mixed polyurea/polyamide, polyurethane, urea/formaldehyde, melamine resin, nylon and gelatin/gelatine-gum Arabic.

Representative pesticidally active ingredients suitable for use as an encapsulated product include acephate, acetochlor, alachlor, *Bacillus sphaericus, Bacillus thuringiensis* delta endotoxins, carbosulfan, clomazone, chlorpyrilos, lambda-cyhalothrin, beta-cypermethrin, cyphenotrhin, diazinon, dichlormid, EPTC, esprocarb, etofenprox, fenitrothion, flurochloridone, furathiocarb, halfenprox, hexace-11-enal, hexadec-13-en-11-ynyl acetate, methoprene, metolachlor, S-metolachlor, parathion, parathion-methyl, permethrin, primiphos-ethyl, tefluthrin and tridec-4-enyl acetate. In one embodiment, the encapsulated pesticidally active ingredient is not tefluthrin.

The term "pesticidally active ingredient" refers to chemicals and biological compositions, such as those described herein, which are effective in killing, preventing, or controlling the growth of undesirable pests, such as, plants, insects, mice, microorganism, algae, fungi, bacteria, and the like. The term may also apply to compounds that control the growth of plants in a desired fashion (for example, a growth regulator), to a compound which mimics the natural systemic activated resistance response found in plant species (for example, a plant activator) or to a compound that reduces the phytotoxic response to a herbicide (for example, a herbicide safener). The pesticidally active ingredients are present in an amount that is biologically effective when the composition is if necessary, diluted in a suitable volume of liquid carrier, e.g., water and, applied to the intended target, e.g., the foliage of a plant or locus thereof or incorporated into or coated onto materials, such as building materials.

There are no particular limitations to the solid formulation aids within the scope of the present application. Formulation aids which remain as solid particles in the liquid compositions are known in the art and include attapulgite, montmorillonite and Kaolin clays, silicas, latexes and titanium dioxide.

The pesticidally effective amount of the active ingredient present in the diluted formulation is preferably that amount that is biologically effective when the composition is ready to be applied to the intended target, e.g. the foliage of a plant or locus thereof, plant propagation material or incorporated into or coated onto materials, such as building materials. As used herein, the term "pesticidally effective amount" means the amount of pesticide compound which adversely controls or modifies the pests. For example, in the case of herbicides, a "herbicidally effective amount" is that amount of herbicide sufficient for controlling or modifying plant growth. Controlling or modifying effects include all deviation from natural development, for example, killing, retardation, leaf burn, albinism, dwarfing and the like. The term plants refers to all physical parts of a plant, including seeds, seedlings, saplings, roots, tubers, stems, stalks, foliage and fruits. In the case of fungicides, the term "fungicide" shall mean a material that kills or materially inhibits the growth, proliferation, division, reproduction, or spread of fungi. As used herein, the term "fungicidally effective amount" or "amount effective to control or reduce fungi" in relation to the fungicidal compound is that amount that will kill or materially inhibit the growth, proliferation, division, reproduction, or spread of a significant number of fungi. As used herein, the terms "insecticide", "nematicide" or "acaracide" shall mean a material that kills or materially inhibits the growth, proliferation, reproduction, or spread of insects, nematodes or acarids, respectively. An "effective amount" of the insecticide, nematicide or acaricide is that amount that will kill or materially inhibit the growth, proliferation, reproduction or spread of a significant number of insects, nematodes or acarides. The concentration of pesticidally active ingredients and the rate of application of the compositions of the invention will depend on a number of factors including, for example, the active ingredients chosen for use, the type and amount of pest to be controlled, plant conditions, soil types, weather and growing conditions, amount of control desired and any applicable label rate restictions. These amounts can readily be determined by following approved label rates for a given pesticide and use thereof as well as by routine experimentation.

While the amounts of pesticidally active ingredients and formulation aids can readily be determined by one skilled in the art, the benefits of the present invention are most clearly recognized when the solid and/or encapsulated pesticidally active ingredients or formulation aids are present in an amount such that if sedimentation occurs the sediment can become hard packed in nature making redispersion or resuspension difficult. The presence of 0.0001 to 10% by weight of a solid or encapsulated pesticidally active ingredient or formulation aid are typical amounts of solid or encapsulated particles present in diluted formulations which can lead to sedimentation and hard packing.

EXAMPLES

An intermediate "capsule base" was prepared by emulsifying an organic phase containing pyrethroid insecticide, solvent and isocyantates in an aqueous phase. Upon shearing and achieving a suitable particle size, the contents were heated so that the isocyanates react interfacially, forming polyurea walls around the pyrethroid and solvent The resultant microcapsule suspension was subsequently cooled and formulated with components such as antifreezes, preservatives and thickeners.

The microcapsule ($D_{95}$=7.5 micrometers, $D_{50}$=3.7 micrometers) formulations were prepared leaving 0.5 wt % blank for addition of various dispersants. Approximately 50 g samples were split from the master batch, and various dispersant or dispersant combinations, as set forth in Table 1, were added to complete 25 different formulations. In addition, a control sample was prepared with no added dispersant, using water to complete the formulation. The samples were vigorously mixed to ensure incorporation of the added dispersants.

Dilution tests were carried out at room temperature using two different levels of water hardness. Using an Eppendorf pipette, 4 mL of each formulation was diluted into 96 mL of water in a 100 mL glass graduated cylinder. 50 ppm and 1000 ppm dilutions were prepared for each formulation, with two sets of each water hardness prepared for evaluation after for hours and sixteen hours. These time intervals were chosen to simulate diluted product standing over a typical "break" for the applicator (4 hours) and overnight (16 hours). The dilutions were inverted 20× and allowed to stand. After standing for the desired time, the cylinders were noted for the volume of settled sediment and subsequently subjected to cycles of inversions until the bottom of the cylinder was visually free of sediment. Inversions were performed manually.

Dispersants evaluated at 0.5 wt % in the formulation included blends (mostly 1/1 by weight) of polyarylphenol ethoxylate phosphates and alkylamine ethoxylates, as well as single component polyarylphenol ethoxylate phosphates, polyarylphenol ethoxylates, and alkylamine ethoxylates. Also included were typical dispersants for agrichemical suspensions such as a block copolymer, anionic polymer dispersant, and lignosulfonates.

TABLE 1

| | | 4 hours | | | | 16 hours | | | |
|---|---|---|---|---|---|---|---|---|---|
| | | Sediment (mL) | | # of Reinversions | | Sediment (mL) | | # of Reinversions | |
| | Dispersant | 50 ppm | 1000 ppm | 50 ppm | 1000 ppm | 50 ppm | 1000 ppm | 50 ppm | 1000 ppm |
| 1 | No dispersant | 0.5 | 0.75 | 36 | 3 | 1 | 2 | 95 | 17 |
| 2* | Cocoamine POE-5/ Polyarylphenol ethoxylate phosphate POE-8 (1/1) | 0.25 | 0.5 | 12 | 6 | 1 | 2 | 29 | 10 |

TABLE 1-continued

|  | Dispersant | 4 hours | | | | 16 hours | | | |
|---|---|---|---|---|---|---|---|---|---|
|  |  | Sediment (mL) | | # of Reinversions | | Sediment (mL) | | # of Reinversions | |
|  |  | 50 ppm | 1000 ppm | 50 ppm | 1000 ppm | 50 ppm | 1000 ppm | 50 ppm | 1000 ppm |
| 3* | Cocoamine POE-5/ Polyarylphenol ethoxylate phosphate POE-8 (7/3) | 0.25 | 0.5 | 10 | 6 | 1 | 2 | 25 | 15 |
| 4 | Tallowamine POE-2/ Polyarylphenol ethoxylate phosphate POE-16 (1/1) | 0.5 | 4 | 32 | 3 | 1 | 4 | 53 | 3 |
| 5 | Cocoamine POE-5/ Polyarylphenol ethoxylate phosphate POE-16 (1/1) | 0.25 | 0.25 | 20 | 11 | 1.5 | 1 | 38 | 17 |
| 6* | Tallowamine POE-2/ Polyarylphenol ethoxylate phosphate POE-8 (1/1) | 0.5 | 4 | 22 | 2 | 1.5 | 5 | 38 | 3 |
| 7* | Tallowamine POE-5/ Polyarylphenol ethoxylate phosphate POE-8 (1/1) | 0.25 | 0.5 | 15 | 6 | 1.5 | 3 | 28 | 9 |
| 8* | Cocoamine POE-2/ Polyarylphenol ethoxylate phosphate POE-8 (1/1) | 0.25 | 4 | 14 | 3 | 1.5 | 5 | 34 | 2 |
| 9 | Cocoamine POE-2/ Polyarylphenol ethoxylate phosphate POE-16 (1/1) | 0.25 | 4 | 24 | 3 | 1 | 5 | 51 | 4 |
| 10 | Cocoamine POE-5/ Polyarylphenol ethoxylate POE-8 | 0.25 | 0.75 | 18 | 6 | 1 | 3 | 42 | 8 |
| 11 | Tallowamine POE-15/ Polyarylphenol ethoxylate phosphate POE-8 (1/1) | 0.25 | 0.5 | 19 | 8 | 2 | 2 | 48 | 15 |
| 12 | Tallowamine POE-15/ Polyarylphenol ethoxylate phosphate POE-16 (1/1) | 0.25 | 0.25 | 24 | 12 | 1.5 | 2 | 65 | 16 |
| 13 | Polyarylphenol ethoxylate phosphate POE-8 | 0.25 | 0.75 | 15 | 3 | 1 | 2 | 43 | 14 |
| 14 | Polyarylphenol ethoxylate phosphate POE-16 | 0.25 | 0.25 | 18 | 16 | 1.5 | 2 | 53 | 29 |
| 15 | Polyarylphenol ethoxylate POE-8 | 0.25 | 0.75 | 30 | 6 | 2 | 2 | 80 | 12 |
| 16 | Polyarylphenol ethoxylate POE-16 | 0.5 | 0.5 | 27 | 20 | 2 | 2 | 86 | 46 |
| 17 | Tallowamine ethoxylate POE-2 | 0.5 | 5 | 18 | 2 | 2 | 5 | 35 | 2 |
| 18 | Tallowamine ethoxylate POE-5 | 0.25 | 0.5 | 18 | 4 | 1 | 3 | 30 | 5 |

TABLE 1-continued

| | | 4 hours | | | | 16 hours | | | |
| | | Sediment (mL) | | # of Reinversions | | Sediment (mL) | | # of Reinversions | |
| | Dispersant | 50 ppm | 1000 ppm | 50 ppm | 1000 ppm | 50 ppm | 1000 ppm | 50 ppm | 1000 ppm |
|---|---|---|---|---|---|---|---|---|---|
| 19 | Tallowamine ethoxylate POE-15 | 0.25 | 0.5 | 16 | 14 | 2 | 2.5 | 50 | 15 |
| 20 | Cocoamine POE-2 | 0.25 | 5 | 16 | 2 | 1 | 5 | 35 | 2 |
| 21 | Cocoamine POE-5 | 0.25 | 0.75 | 19 | 7 | 1.5 | 3 | 38 | 8 |
| 22 | Sodium lignosulfonate | 0.5 | 0.5 | 25 | 15 | 1 | 2.5 | 100 | 30 |
| 23 | Stepsperse 200 (anionic surfactant + Kraft lignosulfonate) | 0.5 | 0.5 | 25 | 16 | 1.5 | 1.5 | 75 | 59 |
| 24 | Stepsperse 400 (nonionic surfactant + Kraft lignosulfonate) | 0.5 | 0.5 | 28 | 13 | 1.5 | 2 | 85 | 32 |
| 25 | Tersperse 2735 (polymeric anionic surfactant) | 0.25 | 1 | 31 | 4 | 1.5 | 3 | 110 | 9 |
| 26 | Toximul 8320 (EO/PO block copolymer) | 0.5 | 0.5 | 28 | 13 | 1.5 | 2 | 100 | 26 |

*Dispersant compositions of the present invention

In this experiment, it is desired to have a dispersant/resuspending agent that will allow for minimal amounts of settled sediment upon standing, while also allowing for resuspension of solids with the least agitation (i.e., reinversions), in both hard and soft waters. Especially relevant, and problematic for many microcapsules is performance in soft water. The data shows that Entries 2, 3 and 7 (compositions of the present invention) provide, on the whole, the best results, taking into account results for both 50 ppm and 1000 ppm water, and at both time intervals. All three entries are combinations of mid-range HLB alkylamine ethoxylates and POE-8 polyarylphenol ethoxylate phosphate.

Similar to the capsule base above, an intermediate prodiamine millbase formulation was prepared by adding prodiamine technical to a stirred aqueous solution containing a wetting agent, a dispersant, an antifoam agent, and an antifreeze agent. This millbase was milled in a horizontal mill to reduce particle size. To this millbase, 1.5% of the dispersants as set forth in Table 2 were added while mixing. The formulation was finished off with the addition of thickeners, a preservative and water.

TABLE 2

| | Dispersant | | | | | | | | |
| | A | B | C | D | E | F | G | H | I |
|---|---|---|---|---|---|---|---|---|---|
| Tristyrylphenol ethoxylate - 8 moles EO | 0 | 0 | 49.5 | 69.5 | 37.6 | 16.9 | 69.8 | 0 | 29.3 |
| Tristyrylphenol ethoxylate phosphate - 8 moles EO | 0 | 100 | 35.5 | 30.5 | 24.4 | 71.1 | 12.2 | 40.6 | 43.7 |
| Cocoamine ethoxyate - 5 moles EO | 0 | 0 | 15 | 0 | 38 | 12 | 18 | 59.4 | 27 |

The number of inversions required to re-suspend the solids 24 hrs post dilution of the formulations containing Dispersant A-I was measured and are set forth in Table 3.

TABLE 3

| Sample | 50 ppm inv | 500 ppm inv |
|---|---|---|
| A | 50+ | 50+ |
| B | 50+ | 11 |
| C | 7* | 10 |
| D | 12* | 12* |
| E | 13 | 9 |
| F | 14 | 11 |
| G | 11 | 9 |
| H | 8 | 13* |
| I | 12 | 11 |

*means there was residue in the edges of the cylinder that never resuspended

Although only a few exemplary embodiments of this invention have been described in detail above, those skilled in the art will readily appreciate that man modifications are possible in the exemplary embodiments without materially departing from the novel teachings and advantages of this

We claim:

1. A composition comprising:
   a) at least one phosphated arylphenol $C_2$-$C_4$ alkoxylate surfactant having an average degree of alkoxylation of from 4-8; and
   b) at least one alkylamine $C_2$-$C_3$ alkoxylate surfactant having an average degree of alkoxylation of from 2-12.

2. The composition of claim 1 wherein component a) is present in an amount of 0.0001 to 95% by weight; and component b) is present in an amount of 0.0001 to 95% by weight of the composition.

3. The composition of claim 2 wherein components a) and b) together are is present in an amount of 20 to 100% by weight.

4. The composition of claim 2 wherein components a) and b) together are is present in an amount of 0.01 to 60% by weight.

5. The composition of claim 2 wherein components a) and b) together are present in an amount of 0.0001 to 10%.

6. The composition of claim 1 wherein components a) and b) are present in a ratio of 20:1 to 1:20.

7. The composition of claim 1 wherein the alkylamine $C_2$-$C_3$ alkoxylate surfactant is an alkylamine ethoxylate having an average degree of ethoxylation of 2 to 5.

8. The composition of claim 7 wherein the alkylamine ethoxylate surfactant comprises cocoamine ethoxylate.

9. A composition comprising at least one solid or encapsulated pesticidally active ingredient or formulation aid and a surfactant composition comprising:
   a) at least one phosphated arylphenol $C_2$-$C_4$ alkoxylate surfactant having an average degree of alkoxylation of from 4-8; and
   b) at least one alkylamine $C_2$-$C_3$ alkoxylate surfactant having an average degree of alkoxylation of from 2-12.

10. The composition of claim 9 wherein the composition comprises a concentrated formulation selected from the group consisting of a capsule suspension, an oil dispersion, an oil flowable, a suspension concentrate, a suspoemulsion and mixtures thereof.

11. The composition of claim 10 wherein surfactants a) and b) are present in the concentrated formulation.

12. The composition of claim 11 comprising 0.01 to 60% by weight of a solid or encapsulated pesticidally active ingredient.

13. The composition of claim 9 wherein the composition is obtained by diluting a concentrated formulation comprising at least one solid or encapsulated pesticidally active ingredient in a liquid carrier, wherein surfactants a) and b), individually, are present in said concentrated formulation, added separately to the liquid carrier or a combination thereof.

14. The composition of claim 13 comprising 0.0001 to 10% by weight of a solid or encapsulated pesticidally active ingredient.

15. The composition of claim 13 wherein at least one of surfactants a) or b) is added to the liquid carrier separate from the concentrated formulation.

16. The composition of claim 9 wherein components a) and b) are present in a ratio of 20:1 to 1:20.

17. The composition of claim 9 wherein the alkylamine $C_2$-$C_3$ alkoxylate surfactant is an alkylamine ethoxylate having an average degree of ethoxylation of 2 to 5.

18. The composition of claim 17 wherein the alkylamine ethoxylate surfactant comprises cocoamine ethoxylate.

19. A composition comprising:
   i) a liquid continuous phase,
   ii) a surfactant composition comprising:
      a) at least one phosphated arylphenol $C_2$-$C_4$ alkoxylate surfactant having an average degree of alkoxylation of from 4-8; and
      b) at least one alkylamine $C_2$-$C_3$ alkoxylate surfactant having an average degree of alkoxylation of from 2-12 and
   iii) a dispersed phase comprising at least one solid or encapsulated pesticidally active ingredient or formulation aid.

20. The composition of claim 19 wherein components a) and b) are present in a ratio of 20:1 to 1:20.

21. The composition of claim 19 wherein the alkylamine $C_2$-$C_3$ alkoxylate surfactant is an alkylamine ethoxylate having an average degree of ethoxylation of 2 to 5.

22. The composition of claim 20 wherein the alkylamine ethoxylate surfactant comprises cocoamine ethoxylate.

23. A method for improving the re-suspension properties of a pesticide suspension comprising forming a composition comprising at least one solid or encapsulated pesticidally active ingredient or formulation aid and a surfactant composition comprising a) at least one phosphated arylphenol $C_2$-$C_4$ alkoxylate surfactant having an average degree of alkoxylation of from 4-8; and b) at least one alkylamine $C_2$-$C_3$ alkoxylate surfactant having an average degree of alkoxylation of from 2-12.

24. The method for improving the re-suspension properties of a pesticide suspension according to claim 23, wherein the surfactant composition comprising a) at least one phosphated arylphenol $C_2$-$C_4$ alkoxylate surfactant having an average degree of alkoxylation of from 4-8; and b) at least one alkylamine $C_2$-$C_3$ alkoxylate surfactant having an average degree of alkoxylation of from 2-12, or at least one component of said surfactant composition, is present in a concentrate comprising the solid or encapsulated, pesticidally active ingredient or formulation aid.

25. The method for improving the re-suspension properties of a pesticide suspension according to claim 23, wherein the surfactant composition comprising a) at least one phosphated arylphenol $C_2$-$C_4$ alkoxylate surfactant having an average degree of alkoxylation of from 4-8; and b) at least one alkylamine $C_2$-$C_3$ alkoxylate surfactant having an average degree of alkoxylation of from 2-12, or at least one component of said surfactant composition, is added to a dilute composition comprising the solid or encapsulated, pesticidally active ingredient formulation aid.

26. The method of 24 wherein the surfactant composition is present in a concentrate comprising the solid or encapsulated, pesticidally active ingredient or formulation aid.

27. The method of 25 wherein the surfactant composition is added to a dilute composition comprising the solid or encapsulated, pesticidally active ingredient formulation aid.

28. The composition of claim 22 wherein components a) and b) together are present in an amount of 0.0001 to 10%.

29. The method of claim 23 wherein the alkylamine $C_2$-$C_3$ alkoxylate surfactant is an alkylamine ethoxylate having an average degree of ethoxylation of 2 to 5.

30. The method of claim 29 wherein the alkylamine ethoxylate surfactant comprises cocoamine ethoxylate.

31. The method of claim 23 wherein components a) and b) are present in a ratio of 20:1 to 1:20.

* * * * *